United States Patent
Combs et al.

(10) Patent No.: US 6,280,703 B1
(45) Date of Patent: Aug. 28, 2001

(54) SIMULTANEOUS MULTIMODAL MEASUREMENT OF PHYSIOLOGICAL FUNCTION

(75) Inventors: Arthur H. Combs; Richard B. Dorshow, both of St. Louis; Joseph E. Bugaj, St. Charles; Raghavan Rajagopalan, Maryland Heights; Samuel I. Achilefu, St. Louis, all of MO (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/519,455

(22) Filed: Mar. 6, 2000

Related U.S. Application Data

(63) Continuation-in-part of application No. 09/258,148, filed on Feb. 26, 1999, which is a continuation-in-part of application No. 08/816,332, filed on Mar. 13, 1997, now Pat. No. 5,928,625.

(51) Int. Cl.[7] .......................... A61K 49/00; G01N 31/00
(52) U.S. Cl. .......................... 424/9.1; 424/1.11; 424/9.6
(58) Field of Search ................................ 424/1.11, 9.1, 424/9.2, 9.3, 9.4, 9.5, 9.6, 9.7, 9.8; 534/7, 10–16

(56) References Cited

U.S. PATENT DOCUMENTS

| | | |
|---|---|---|
| 4,848,349 | 7/1989 | Sherman et al. . |
| 4,905,703 | 3/1990 | Kanda et al. . |
| 5,054,915 | 10/1991 | Kanda et al. . |
| 5,054,916 | 10/1991 | Kanda et al. . |
| 5,178,141 | 1/1993 | Kanda . |
| 5,301,673 | 4/1994 | Rabito et al. . |
| 5,458,128 | 10/1995 | Polanyi et al. . |
| 5,647,363 | 7/1997 | Rabito et al. . |
| 5,845,639 * | 12/1998 | Hochman et al. ................. 128/653.1 |
| 5,928,625 | 7/1999 | Dorshow et al. . |
| 6,123,921 * | 9/2000 | Meade et al. ..................... 424/9.363 |

FOREIGN PATENT DOCUMENTS

| | | |
|---|---|---|
| 4445065 | 6/1996 | (DE) . |
| 9706829 | 2/1997 | (WO) . |

OTHER PUBLICATIONS

Awazu, K. et al. "The data processing function of the ICG clearance meter", 1992: Abstract—1 page, Yakuri to Chiryo, 20 (10).

Bilheimer, D.W. et al. "Metabolic Studies in Familial Hypercholesterolemia", *J. Clin. Invest.*, Aug. 1979; 64:524–533.

Graham, B.H. et al. "Serial quantitative skin surface fluorescence: A new method for postoperative monitoring of vascular perfusion in revascularized digits", *The Journal of Hand Surgery*, 1985: 10A:226–30.

Caesar, J. et al. "The Use of Indocyanine Green in the Measurement of Hepatic Blood Flow and as a Test of Hepatic Function", *Clin. Sci.*, 1961; 21:43–57.

Flock, S. T. et al. "Optical Properties of Intralipid: A Phantom Medium for Light Propagation Studies", *Lasers in Surgery and Medicine*, 1992; 12:510–519.

Hemming, A.W. et al. "Indocyanine Green Clearance as a Predictor of Successful Hepatic Resection in Cirrhotic Patients", *The American Journal of Surgery*, May 1992; 163:515–518.

Hollins, B. et al. "Fluorometric Determination of Indocyanine Green in Plasma", *Clin. Chem.*, 1987; 33(6):765–768.

Jalan, R. et al. "Review article: quantitative tests of liver function", *Aliment Pharmacol. Ther.*, 1995; 9:263–270.

Kanaya, N. et al. "Comparison of the effects of sevoflurane, isoflurane and halothane on indocyanine green clearance", *British Journal of Anaesthesia*, 1995, 74:164–167.

Kanaya, N. et al. "Noninvasive ICG clearance test for estimating hepatic blood flow during halothane and isoflurane anaesthesia", *Can. J. Anaesth.*, 1995; 42(3):209–212.

Kanda, M. et al. "Continuous monitoring of Cardiogreen removal by a diseased liver using an optical sensor", *SPIE*, 1988; 904:39–46.

Kudo, M. et al. "Receptor Index via Hepatic Asialoglycoprotein Receptor Imaging: Correlation with Chronic Hepatocellular Damage", *American Journal of Gastroenterology*, 1992; 87(7):865–870.

Li, X. et al. "Tumor Localization Using Fluorescence of Indocyanine Green (ICG) in Rat Models", *SPIE*, 1995; vol. 2389, pp. 789–797.

Mordon, S. et al. "Fluorescence measurement of diode (805nm) laser–induced release of 5,6–CF from DSPC liposomes for monitoring of temperature: an in–vivo study in rat liver using indocyanine green potentiation", *SPIE*, 1995; vol. 2391, pp. 475–483.

Nakayama, M. et al. "Effects of Ephedrine on Indocyanine Green Clearance During Spinal Anesthesia: Evaluation by the Finger Piece Method", *Anesth. Analg.*, 1993; 77:947–949.

O'Leary, M.A. et al. "Reradiation and imaging of diffuse photon density waves using fluorescent inhomogeneities", *Journal of Luminescence*, 1994; 60&61:281–286.

(List continued on next page.)

Primary Examiner—Dameron L. Jones
(74) Attorney, Agent, or Firm—Rothwell, Figg, Ernst & Manbeck

(57) ABSTRACT

A method of measuring physiological function of a group of body cells, includes the step of selecting a detectable agent capable of absorbing or emitting a measurable electromagnetic emission. The agent is introduced into body fluid which contacts the group of body cells. The absorbance or emission is measured, and physiological function is determined based on measurement of the absorbance or emission. Measurements may be made noninvasively or with the use of a modified pulmonary artery catheter. Multiple agents which can be distinguished from each other can be utilized simultaneously to measure multiple physiological functions at the same time.

28 Claims, 4 Drawing Sheets

OTHER PUBLICATIONS

Ott, P. et al. "Plasma Elimination of Indocyanine Green in the Intact Pig After Bolus Injection and During Constant Infusion: Comparison of Spectrophotometry and High–pressure Liquid Chromatography for Concentration Analysis", *Hepatology*, 1993; 18(6):1504–1515.

Scott, V.L. et al. "Comparison of indocyanine green clearance using serum spectrophotometric analysis and a non–invasive pulse–spectrometry probe in patients with liver failure", Annual Meeting of the American Society of Anesthesiologists, San Diego, CA, Oct. 18–22, 1997, 1 page Abstract.

Sheridan, R.L. et al. "Burn Depth Estimation by Use of Indocyanine Green Fluorescence: Initial Human Trial", *J. Burn Care Rehabil.*, 1995; 16:602–604.

Shimizu, S. et al. "New Method for Measuring ICG Rmax with a Clearance Meter", *World J. Surg.*, 1995; 19:113–118.

Shinohara, H. et al. "Direct Measurement of Hepatic Indocyanine Green Clearance With Near–Infrared Spectroscopy: Separate Evaluation of Uptake and Removal", *Hepatology*, 1996; 23:137–144.

Soulie, S. et al. "In vivo pharmacokinetic study of two fluorescein derivatives by fluorescence spectroscopy", *SPIE*, 1995; vol. 2627, pp. 109–117.

Tsai, K.–N. et al. "Comparison of ICG Finger Monitor system with conventional blood sampling ICG clearance test in patients with acute severe hepatitis", *Gastroenterological Journal of Taiwan*, 1996; 1 page Abstract.

Urata, K. et al. "Clinical evaluation of indocyanine green clearance using the finger–piece method in patients undergoing hepatic surgery", 1992; 1 page Abstract, Yakuri to Chiryo, 20 (10).

\* cited by examiner

SIMULTANEOUS MULTIMODAL MEASUREMENT OF PHYSIOLOGICAL FUNCTION

CROSS REFERENCE TO RELATED APPLICATIONS

This application is a continuation-in-part of U.S. patent application Ser. No. 09/258,148, filed Feb. 26, 1999, which is a continuation-in-part of U.S. patent application Ser. No. 08/816,332, filed Mar. 13, 1997, now U.S. Pat. No. 5,928,625, all of which are incorporated herein by reference.

BACKGROUND OF THE INVENTION

1. Field of the Invention

The present invention is in the field of biomedical optics. In particular, this invention pertains to the measurement of physiological function of multiple organs or tissues at once.

2. Description of the Background Art

Simultaneous assessment of physiological function of many organs at the same time is always desirable and often necessary. It is particularly important in the case of critically ill or injured patients because a large percentage of these patients face the risk of multiple organ failure (MOF) resulting in death (C. C. Baker et al., Epidemiology of Trauma Deaths, *American Journal of Surgery*, 1980, 144–150; R. G. Lobenhoffer et al., Treatment Results of Patients with Multiple Trauma: An Analysis of 3406 Cases Treated Between 1972 and 1991 at a German Level I Trauma Center, *Journal of Trauma*, 1995, 38, 70–77). MOF is a sequential failure of lung, liver, and kidneys and is incited by one or more severe causes such as acute lung injury (ALI), adult respiratory distress syndrome (ARDS), hypermetabolism, hypotension, persistent inflammatory focus, or sepsis syndrome. The common histologic features of hypotension and shock leading to MOF include tissue necrosis, vascular congestion, interstitial and cellular edema, hemorrhage, and microthrombi. These changes affect the lung, liver, kidneys, intestine, adrenal glands, brain, and pancreas (in descending order of frequency) (J. Coalson, Pathology of Sepsis, Septic Shock, and Multiple Organ Failure. In *New Horizons: Multiple Organ Failure*, D. J. Bihari and F. B. Cerra, (Eds). *Society of Critical Care Medicine*, Fullerton, Calif., 1986, pp 27–59). The transition from early stages of trauma to clinical MOF is marked by the extent of liver and renal failure and a change in mortality risk from about 30% to about 50% (F. B. Cerra, Multiple Organ Failure Syndrome. In *New Horizons: Multiple Organ Failure*, D. J. Bihari and F. B. Cerra, (Eds). *Society of Critical Care Medicine*, Fullerton, Calif., 1989, pp 1–24).

Hepatic function (i.e., liver function) is difficult to assess in any patient population and particularly in the critically ill population. Currently no measure of "liver function" such as serum transaminase serum GGT, or serum alkaline phosphatase actually indicates the real-time function of the liver or its enzyme systems. Moreover, other tests such as serum glucose, prothrombin time, serum albumin, serum bilirubin, and others indicate the function of the liver on a longer time scale and do not necessarily correlate with immediate clinical conditions. Other studies have shown that even in normal patients other interventions commonly performed in the intensive care unit, such as mechanical ventilation, can adversely affect liver function even in the absence of true hepatic injury. Additionally, "liver function" is actually the conglomeration of many different functions depending on many different enzyme and cellular systems within the liver.

Current clinical practice for the assessment of liver function is based solely upon intermittent blood sampling and the measurement of numerous circulating enzymes and other chemical entities which indirectly imply the nature of both synthetic and elimination functions of the liver. These include coagulation tests, measurements of serum albumin, measurement of serum bilirubin and its conjugated form, and the measurement of serum values for enzymes known to be contained within hepatocytes and bile canalicular cells (J. B. Henry (Ed). *Clinical Diagnosis and Management by Laboratory Methods*, 17th Edition, W. B. Saunders, Philadelphia, Pa., 1984); G. P. Zaloga and D. S. Prough, Monitoring Hepatic Function, *Critical Care Clinics*, 1988, 4, 591–603; W. D. Figg et al., Comparison of Quantitative Methods to Assess Hepatic Function: Pugh's Classification, Indocyanine Green, Antipyrine, and Dextromethorphan, *Pharmacotherapy*, 1995, 15, 693–700; R. Jalan and P. C. Hayes, Quantitative Tests of Liver Function, *Aliment Pharmacol. Ther.*, 1995, 9, 263–270). However, these data are discontinuous, have no real-time implications, are cumbersome to repeat, and can, under certain circumstances (such as in patients with cirrhosis), be extremely misleading. For example, patients with previously healthy livers who take in a toxic ingestion may have profound elevations in serum transaminases but still may have significantly preserved liver function. Conversely, patients with cirrhosis may suffer a serious hepatic insult with minimal elevation in their serum transaminases and yet have almost no hepatic reserve. Additionally, there are patients whose changing hepatic function is key both to their management and ultimately to their survival. These include patients with toxic ingestion and patients with deteriorating liver function for other reasons such as porto-systemic encephalopathy, TIPPS placement, and simple mechanical ventilation which is known to specifically affect the elimination function of the liver.

As mentioned previously, earlier attempts to measure hepatic function by determining the serum concentration of exogenous chemical entities such as bromosulfalein or indocyanine green (J. Caesar et al., The Use of Indocyanine Green in the Measurement of Hepatic Blood Flow and as a Test of Hepatic Function, *Clin. Sci.*, 1961, 21, 43–57; A. W. Hemming et al., Indocyanine Green Clearance as a Predictor of Successful Hepatic Resection in Cirrhotic Patients, *Am. J. Surg.*, 1992, 163, 515–518) were non-specific, singular, and required intermittent blood sampling for assessment. Subsequently, non-invasive techniques for assessing hepatic function by continuously monitoring indocyanine green (ICG) clearance from blood have been developed by us and by others and references describing these techniques are incorporated herein by reference (C. M. Leevy et al., Indocyanine Green Clearance as a Test for Hepatic Function: Evaluation by Dichromatic Ear Densitometry, *Journal of Medicine*, 1993, 24, 10–27; M. Kanda et al., Continuous Monitoring of Cardiogreen Removal by a Diseased Liver Using an Optical Sensor, *Proc. SPIE*, 1988, 904, 39–46; M. Kanda and S. Niwa, Development of a Noninvasive Monitoring Instrument for Serum Indocyanine Green Dye Concentration", *Applied Optics*, 1992, 31, 6668–6675; S. Shimizu et al., A New Method for Measuring ICG Rmax with a Clearance Meter, *World J. Surg.*, 1995, 19, 113–118; R. B. Dorshow et al., Non-Invasive Fluorescence Detection of Hepatic and Renal Function, *Bull. Am. Phys. Soc.* 1997, 42, 681).

Serum creatinine measured at frequent intervals by clinical laboratories is currently the most common way of assessing renal function and following the dynamic changes in renal function which occur in critically ill patients (J. B. Henry (Ed). *Clinical Diagnosis and Management by Labo-* ratory Methods, 17th Edition, W. B. Saunders, Philadelphia, Pa., 1984); C. E. Speicher, *The right test: A physician's guide to laboratory medicine*, W. B. Saunders, Philadelphia, Pa., 1989). These values are frequently misleading since the value is affected by age, state of hydration, renal perfusion, muscle mass, dietary intake, and many other anthropometric and clinical variables. Further, a single value returned several hours after sampling is difficult to correlate with other important physiologic events such as blood pressure, cardiac output, state of hydration and other specific clinical events (e.g., hemorrhage, bacteremia, ventilator settings and others). An approximation of glomerular filtration rate can be made via a 24 hour urine collection. This requires 24 hours to collect, several more hours to analyze, a serum sample at some point in the 24 hours, and meticulous bedside collection technique. New or repeat data are equally cumbersome to obtain. At times, changes in serum creatinine must be further clarified by values for urinary electrolytes, osmolality, and derived calculations such as the "renal failure index" or the "fractional excretion of sodium." These require additional samples of serum collected contemporaneously with urine samples and, after a delay, precise calculations. Many times, dosing of medication is adjusted for renal function and thus can be equally as inaccurate, equally delayed, and as difficult to reassess as the values upon which they are based. Lastly, clinical decisions in the critically ill population are often equally as important in their timing as they are in their accuracy.

Thus the availability of a real-time, accurate, repeatable measure of glomerular filtration rate under specific yet changing circumstances represents a substantial improvement over any currently available or widely practiced method. Moreover, since the method depends solely on the renal elimination of the exogenous chemical entity, the measurement is absolute and requires no subjective interpretation based on age, muscle mass, blood pressure, etc. In fact it represents the nature of renal function in this particular patient, under these particular circumstances, at this precise moment in time.

Recently, assessment of renal function by continuously monitoring the blood clearance of exogenous optical, radiometric, or magnetic markers such as fluorescein-inulin and fluorescein-succinylated polylysine conjugates, chromium-51 ethylenediamine tetraacetate complex, and gadolinium diethylenetriamine pentaacetate complex have been developed by us and by others and are incorporated herein as reference (R. B. Dorshow et al., Non-Invasive Fluorescence Detection of Hepatic and Renal Function, *Bull. Am. Phys. Soc.* 1997, 42, 681); M. F. Tweedle et al., A Noninvasive Method for Monitoring Renal Status at Bedside, *Investigative Radiology*, 1997, 32, 802–805; M. Sohtell et al., FITC-Inulin as a Kidney Tubule Marker in the Rat, *Acta. Physiol. Scand.*, 1983, 119, 313–316; and M. Rehling et al., Simultaneous Measurement of Renal Clearance of $^{99m}$Tc-Labelled Diethylenetriamine-pentaacetic acid, $^{51}$Cr-labelled Ethylenediamine-tetraacetate and Inulin in Man, *Clin. Sci.*, 1984, 66, 613–619).

Thus, there remains a need in the art for methods of measuring physiological function of many organs at once to reduce the risk of fatality due to multiple organ failure.

In addition, the invention may also be used to evaluate hypercholesterolemia. Clearance rate measurements may allow the clinician to determine whether high serum cholesterol resulted from increased rate of LDL production or from decreased rate of LDL clearance, which may impact therapy. The invention may also be used to measure cardiac output. The ability to concurrently measure cardiac function while also measuring hepatic and renal function may allow the clinician to draw preliminary conclusions about whether any observed changes in hepatic and renal functions were due to primary renal or hepatic disease or secondary to heart disease.

SUMMARY OF THE INVENTION

In accordance with the present invention, a method of simultaneously measuring physiological functions of multiple groups of body cells, includes the step of selecting two or more detectable agents, hereinafter referred to as 'tracers,' capable of absorbing or emitting electromagnetic radiation at different wavelengths. The tracers are selected from the group consisting of chromophores, fluorophores, paramagnetic agents, radionuclides, echogenic agents, or any bioconjugates derived from these tracer molecules. The tracers are introduced into body fluid which contacts the group of body cells. The absorption or emission is detected by the standard invasive or non-invasive methods known in the art, and physiological function is correlated with the clearance profiles and rates of these agents from the body fluids. One important aspect of the present invention is that the detectable agents act independently of each other in vivo and do not adversely affect the clearance rate or profile of other agents. This property has been demonstrated as described in the Examples. The distinctive feature of the present invention is that it discloses a method of performing diagnostic procedures of multiple organ functions using multiple modalities. The prior art methods, including a recent one disclosing a combination of an optical dye and a paramagnetic chelate linked to a polymer (T. J. Meade et al., Bifunctional Detector Agent Having a Polymer Covalently Linked to an MRI Agent and an Optical Dye, U.S. Pat. No. 5,900,228, 1999), employ either a single or a dual modality for diagnosis of one organ or one type of tissue at a time or a single modality to diagnose one or more tissues at a time (C. A. Rabito et al., Ambulatory Clearance Function Monitor, U.S. Pat. No. 5,301,673). The prior art methods do not suggest a combination of multiple modalities for multiple organ functions.

The absorption or emission can be measured using non-invasive or invasive techniques. Invasive techniques include using endoscopes and catheters inserted into the respective body portion. Non-invasive techniques include surface probes such as ear clips, hand bands, surface coils, finger probes, and the like. The methods of the instant invention are advantageous over the prior art because of the capability of assessing the viability of multiple organs or tissues at the same time leading to better patient care management and reducing the risk of multiple organ failure.

DETAILED DESCRIPTION OF THE INVENTION

Figure 1:
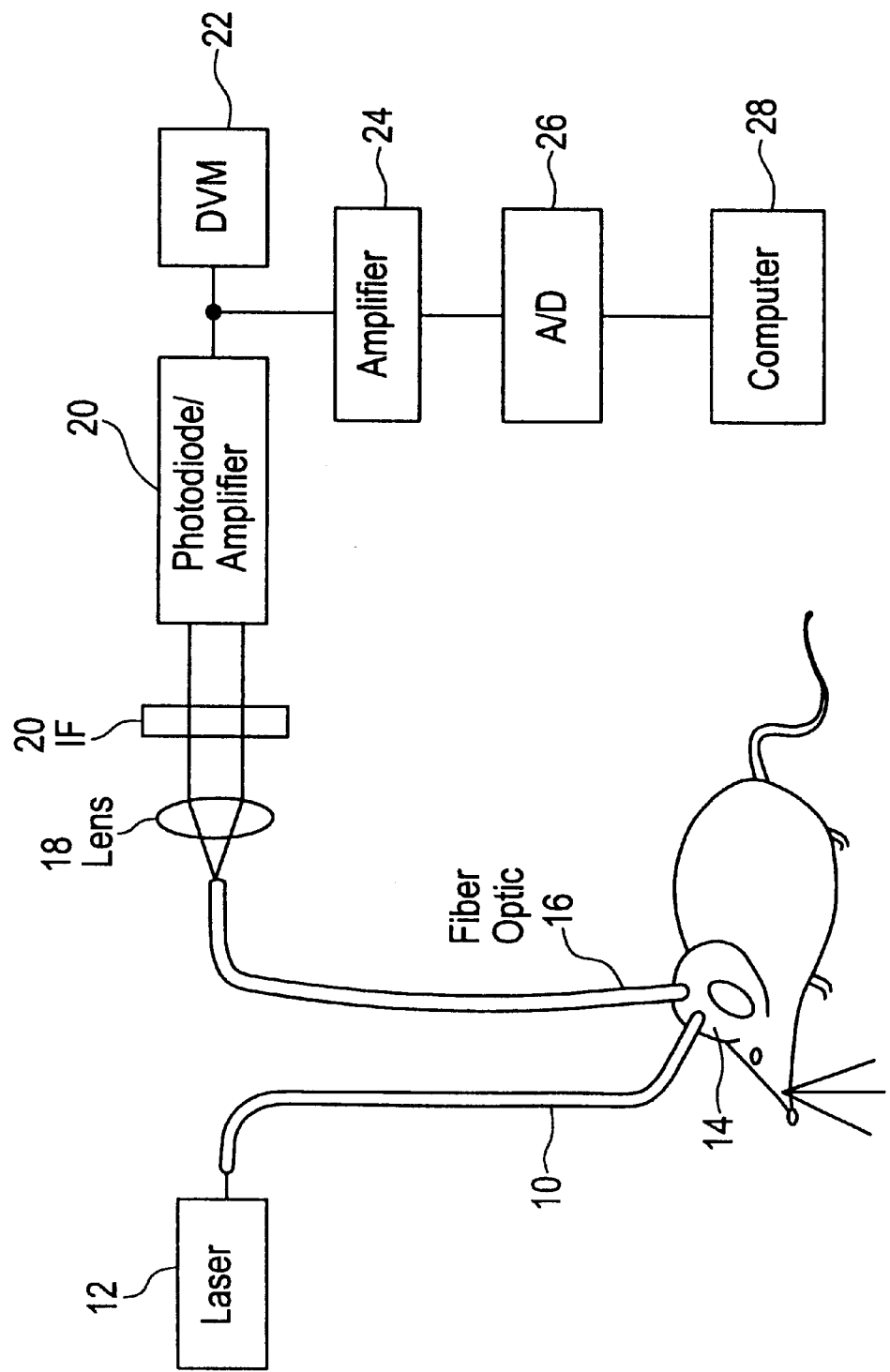
FIG. 1 is a schematic illustration of an in vivo fluorescence detection apparatus in accordance with one embodiment.

In accordance with the present invention, a method is disclosed for determining multiple organ functions or activities by measuring the blood clearance of exogenous entities, hereinafter referred to as 'tracers,' selected from the group consisting of chromophores, fluorophores, paramagnetic agents, radiographic agents, X-ray contrast agents, and echogenic agents. The tracers may be introduced into the patient by any suitable method, including intravenous, intraperitoneal, or subcutaneous injection or infusion, oral administration, transdermal absorption through the skin, or by inhalation.

The detection of the tracers can be achieved by radiometric, magnetic, ultrasonic, or optical methods known in the art. If an optical method is desired, then the measurement of its clearance or accumulation can be made by administering a detectable amount of dyes such as indocyanine green, fluorescein, rhodamine, and the like and using an invasive or non-invasive optical procedure as described by Dorshow et al. (Non-Invasive Fluorescence Detection of Hepatic and Renal Function, *Bull. Am. Phys. Soc.* 1997, 42, 681 or by Kanda et al. (Liver Function Testing Apparatus, U.S. Pat. No. 5,178,141, 1993). The detection method includes absorbance, fluorescence, or light scattering techniques well known in the art (Muller et al. (Eds.), Medical Optical Tomography, SPIE Volume IS11, 1993). If a radiometric method is desired, then the measurement can be made by administering a detectable amount of radiopharmaceutical compounds such as $^{99m}$Tc-DTPA, $^{51}$Cr-EDTA, $^{99m}$Tc-MAG3, $^{99m}$Tc-HIDA, $^{99m}$Tc-sestamibi, $^{99m}$Tc-tetrafosmin, $^{99m}$Tc-ECD, $^{131}$I-hippuran, $^{99m}$Tc-DTPA-octreotide, $^{99m}$Tc-DTPA-octreotate, and the like and using a non-invasive 'arm-band' radiometric procedure as described by Rabito et al. (Ambulatory Clearance Function Monitor, U.S. Pat. No. 5,301,673, 1994). If a magnetic method is desired, then the measurement can be made by administering a detectable amount of paramagnetic agents such as gadolinium complexes or superparamagnetic particles and using a magnetic resonance procedure as described by Tweedle et al. (A Noninvasive Method for Monitoring Renal Status at Bedside, *Investigative Radiology*, 1997, 32, 802–805).

In a preferred embodiment, the method of assessing multiple organ functions or activities comprises the following: selection of two or more chromophores or fluorophores from the group consisting of dyes capable of absorbing or emitting visible or near-infrared light with the wavelength ranging from 400 to 900 nm; administration of a detectable amount of the tracer intravenously into the patient's body; and the detection of the signals using invasive or non-invasive optical probes and devices.

In another preferred embodiment, the method of assessing multiple organ functions or activities comprises the following: selection of two or more radiopharmaceutical agents from the group consisting of $^{99m}$Tc-DTPA, $^{51}$Cr-EDTA, $^{99m}$Tc-MAG3, $^{99m}$Tc-HIDA, or $^{131}$I-hippuran; administration of a detectable amount of the tracers intravenously in to the patient's body; and the detection of the signals using non-invasive radiometric probes and devices.

In another preferred embodiment, the method of assessing multiple organ functions or activities comprises the following: selection of two or more paramagnetic agents from the group consisting of Gd-DTPA, Gd-DTPA-bis(methoxyethyl)amide, or superparamagnetic iron oxide particles; administration of a detectable amount of the tracers intravenously into the patient's body; and the detection of the signals using non-invasive magnetic resonance probes and devices.

In another preferred embodiment, the method of assessing multiple organ functions or activities comprises the following: selection of one or more chromophores or fluorophores from the group consisting of dyes capable of absorbing or emitting visible or near-infrared light with the wavelength ranging from 400 to 900 nm, and one or more radiopharmaceutical agents $^{99m}$Tc-DTPA, $^{51}$Cr-EDTA, $^{99m}$Tc-MAG3, $^{99m}$Tc-HIDA, or $^{131}$I-hippuran; administration of a detectable amount of the tracers intravenously into the patient's body; and the detection of the signals using invasive or non-invasive optical and radiometric probes and devices.

In another preferred embodiment, the method of assessing multiple organ functions or activities comprises the following: selection of one or more chromophores or fluorophores from the group consisting of dyes capable of absorbing or emitting visible or near-infrared light with the wavelength ranging from 400 to 900 nm, and one or more paramagnetic agents from the group consisting of Gd-DTPA, Gd-DTPA-bis(methoxyethyl)amide, or superparamagnetic iron oxide particles; administration of a detectable amount of the tracers intravenously into the patient's body; and the detection of the signals using invasive or non-invasive optical and magnetic resonance probes and devices.

In another preferred embodiment, the method of assessing multiple organ functions or activities comprises the following: selection of one or more paramagnetic agents from the group consisting of Gd-DTPA, Gd-DTPA-bis(methoxyethyl)amide, or superparamagnetic iron oxide particles, and one or more radiopharmaceutical agents $^{99m}$Tc-DTPA, $^{51}$Cr-EDTA, $^{99m}$Tc-MAG3, $^{99m}$Tc-HIDA, or $^{131}$I-hippuran; administration of a detectable amount of the tracers intravenously into the patient's body; and the detection of the signals using invasive or non-invasive magnetic resonance and radiometric probes and devices.

The organ functions can be assessed either by the differences in the manner in which the normal and impaired cells remove the tracer from the bloodstream or by measuring the rate or accumulation of these tracers in the tissues or organs of interest. Blood pool clearance may be measured non-invasively from convenient surface capillaries such as those found in an ear lobe or a finger or can be measured invasively using an endovascular catheter. Accumulation of the tracer within the cells of interest can be assessed in a similar fashion. The present invention may be used for rapid bedside evaluation of biologic functions. For example, data on cardiac output, cause of hypercholesterolemia, as well as renal and hepatic function, may be obtained in less than sixty minutes at the bedside after a single intravenous injection. Cardiac output may be determined utilizing the present invention in conjunction with known methods such as the Fick principle. Glomerular filtration may be determined by clearance of a hydrophilic neutral or anionic compound such as a fluorescent agent such as fluorescein-succinylated poly-d-lysine, fluorescein-polyaspartic acid or fluorescein-inulin, or agents such as $^{99m}$Tc-MAG3 or Gd-DTPA. Whether hypercholesterolemia is caused by poor LDL clearance may be determined by analyzing the clearance of fluorescein-labeled LDL. Hepatic function may be assessed by measuring the clearance rate of a fluorescent-labeled asialoglycoprotein or a dye such as indocyanine green, $^{99m}$Tc-HIDA, or superparamagnetic iron oxide particles. Thus, simultaneous assessment of renal or hepatic function by in vivo detection is encompassed within the invention. The invention can also be used to monitor the efficiency of hemodialysis. Tumor cells or brain cells also can be targeted in accordance with the invention.

The clearance of a plurality of separate tracer dyes may be determined simultaneously by selecting excitation wavelengths and filters for the emitted photons. The concentration/time curves may be analyzed in real time by a microprocessor. The resulting clearance rates may be calculated and displayed for immediate clinical impact. In cases where unlabeled competing compounds are present (e.g., LDL, asialoglycoproteins), a single blood sample may be analyzed for the concentration of these competing compounds and the results used to calculate a flux (micromoles/minute) through the clearance pathways.

In order to demonstrate utility of the invention, a non-invasive fluorescence detection system in accordance with the present invention was employed to continuously monitor dye removal from the vasculature. Differentiation between normal and abnormal organ function in a rat model was demonstrated for both liver and kidney. With reference to FIG. 1, a fiber optic 10 transmitted light from source 12 to ear 14. A second fiber optic 16 positioned near the ear 14 transmitted the fluorescent light to a detector system 20. The dyes were intravenously injected. A body portion, which included blood vessels near the surface of the skin, was irradiated with a laser.

Figure 2:
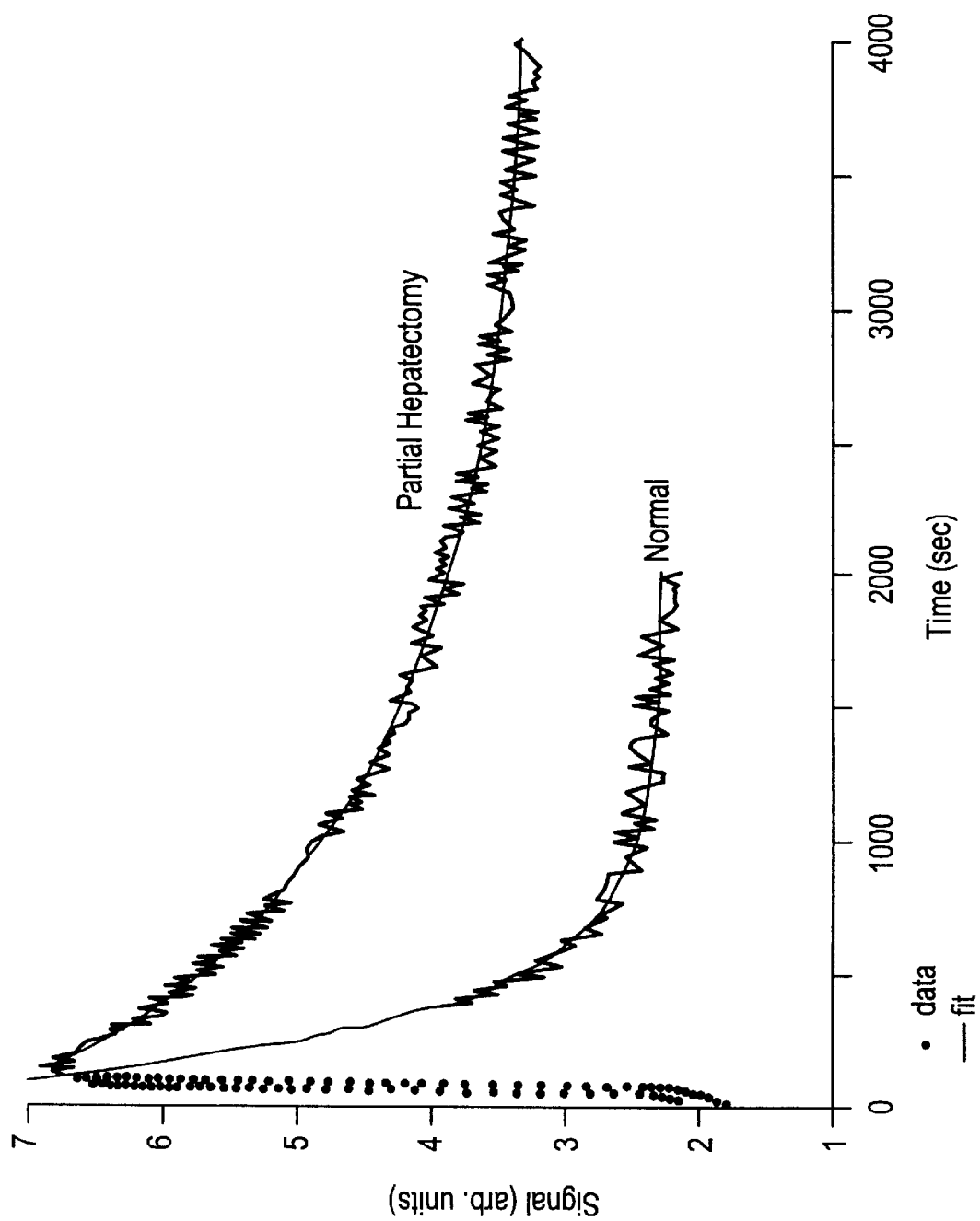
FIG. 2 shows the blood clearance profile of indocyanine green dye in a normal and a partially hepatectomized rat for the assessment of liver function.

Indocyanine green, an optical tracer agent, is known to be exclusively cleared from the blood stream by the liver. A characteristic clearance curve of normal hepatic function was obtained upon excitation in vivo with laser light at 780 nm and detection of the fluorescence signal at 830 nm. Upon ablation of a portion of the liver, the measurement was performed again and the clearance curve was greatly extended as expected (shown in FIG. 2). Thus, a measure of liver function may be assessed with this technique employing a single optical tracer agent.

Figure 3:
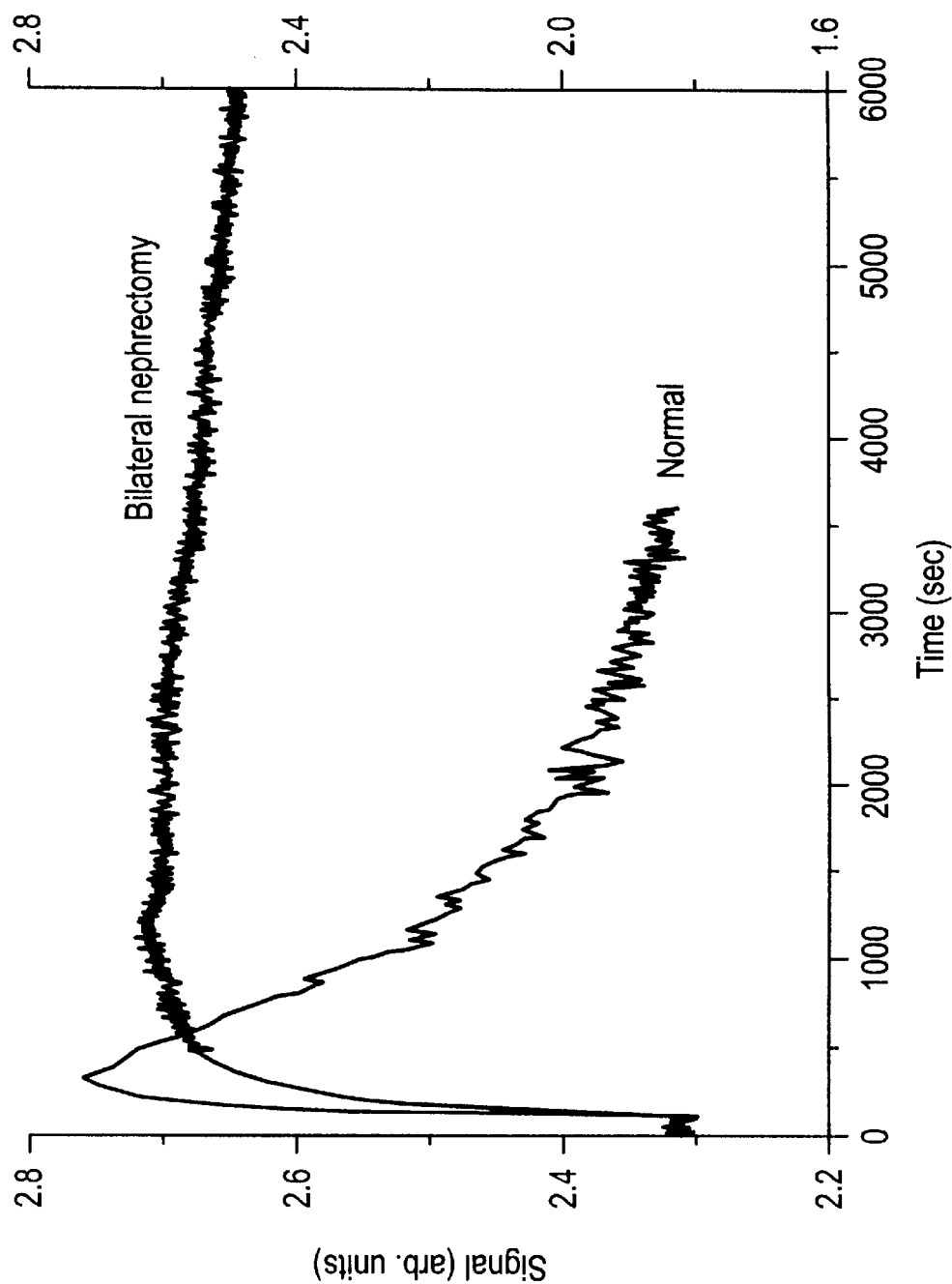
FIG. 3 shows the blood clearance profile of fluorescein-polyaspartate (MW 10,000) conjugate in a normal and a bilaterally nephrectomized rat for the assessment of renal function.

Renal function was measured using the above-described method of the invention. Fluorescein labeled polyaspartic acid was excited in vivo with laser light at 488 nm. The fluorescence signal was detected at 520 nm. A characteristic clearance curve of normal renal function was obtained. Upon ligation of both kidneys, the clearance curve remained elevated and constant, indicating little if any clearance (shown in FIG. 3). Thus, a measure of renal function may be assessed with this technique employing a single optical tracer agent.

In addition to the noninvasive techniques, a modified pulmonary artery catheter can be used to make the necessary measurements. Currently, pulmonary artery catheters measure only intravascular pressures, cardiac output and other derived measures of blood flow. Critically ill patients are managed using these parameters but relying on intermittent blood sampling and testing for assessment of renal function. These laboratory parameters represent discontinuous data and are frequently misleading in many patient populations. Yet, importantly, they are relied upon heavily for patient assessment, treatment decisions, and drug dosing. Currently, no reliable, repeatable bedside method for the assessment of specific renal function (i.e., glomerular filtration rate (GFR)) exists.

The modified pulmonary artery catheter incorporates an optical sensor into the tip of a standard pulmonary artery catheter. This wavelength specific optical sensor can monitor the renal function specific elimination of a designed optically detectable chemical entity. Thus, by a method analogous to a dye dilution curve, real-time renal function can be monitored by the disappearance of the optically detected compound. Modification of a standard pulmonary artery catheter only requires making the fiber optic sensor wavelength specific. Catheters currently exist which incorporate fiber optic technology for measuring mixed venous oxygen saturation.

A variety of dyes and dye-conjugates can be used for the disclosed methods. Dyes which can be used include phenylxanthenes (e.g., fluorescein), phenothiazines, phenoselenazines, cyanines, indocyanines, and squaraines. Preferred carriers are physiologically acceptable polyanionic compounds which may be conjugated to the above dyes. Carriers which can be used include polyacrylic acid, polyaspartic acid, polyglutamic acid, polynucleotides, polyarginine, polyserine, polyornithine, and polylysine.

Use of a mixture of optically detectable chemical entities administered by single injection allows detection by the optical sensors on a standard pulmonary artery catheter thereby giving the clinician a real-time assessment of many important liver functions. These liver functions can represent the detoxification, metabolism, and hepatic elimination functions in particular. The synthetic functions of the liver such as serum albumin, coagulation factors, glucose and others can continue to be assessed by ordinary laboratory testing. However, the concern about appropriate doses of hepatically metabolized and/or eliminated medications including analgesics, anti-arrhythmics, antibiotics, toxins, overdoses, psychotherapeutics, and many others can be much better predicted knowing the status of liver function in these specific regards.

The invention is further illustrated by the following examples, which are not intended to be limiting.

EXAMPLE 1

Use of a Modified Pulmonary Artery Catheter to Measure Renal Function

A standard pulmonary artery catheter is modified by making the fiber optic sensor specific for the desired wavelength to measure fluorescence, absorbance or light scattering. Catheters currently exist which incorporate fiber optic technology for measuring mixed venous oxygen saturation. An optically detectable indicator is bonded to a specific ligand, e.g., one with exclusive renal elimination. The indicator-ligand complex is injected into the patient and readings are made with the modified pulmonary artery catheter. Elimination of the complex is followed by a standard curve generated by the wavelength specific optical sensor and translated by a specific computer algorithm into real-time GFR. The experiments are very similar to the experiments described above except that here a modified pulmonary artery catheter is used to detect the signal rather than using a noninvasive detector.

EXAMPLE 2

Use of a Modified Pulmonary Artery Catheter to Measure Hepatic Function

Modification of a pulmonary artery catheter by addition of one or more optical sensors of specific wavelength to the tip of the catheter allows the catheter to be used for real-time measurements of hepatic function. Pulmonary artery catheters currently exist with optical sensors on them specific for measuring mixed venous oxygen saturation. This is achieved through fiber optic technology and can easily be adapted to other wavelengths.

A second important component is the design of optically detectable molecules with ligands specific for particular hepatic enzyme systems (i.e., liver functions). Thus, the elimination of these dye molecules from the circulation as detected by the sensors on the pulmonary artery catheter represent a simple dye dilution curve. They do, however, have the capacity to represent real-time liver function in terms of specific liver enzyme systems and liver specific elimination.

The injection of and elimination of the optically detectable chemical entities are detected by the optical sensor or sensors which have been added to the pulmonary artery catheter. These molecules are designed to have both a hepatic function specific ligand and an optically detectable moiety. Thus, using technology exactly analogous to the dye dilution curve, the injection of a single optically detectable compound or a mixture of optically detectable compounds and the observance of their elimination can indicate specific hepatic function or functions. The mixture of optically detectable entities can be designed to measure the activity of specific enzyme systems and thus correlate with the anticipated metabolism and/or elimination of important clinical entities such as drugs and chemicals requiring either hepatic metabolism and/or specific hepatic elimination.

EXAMPLE 3

Figure 4:
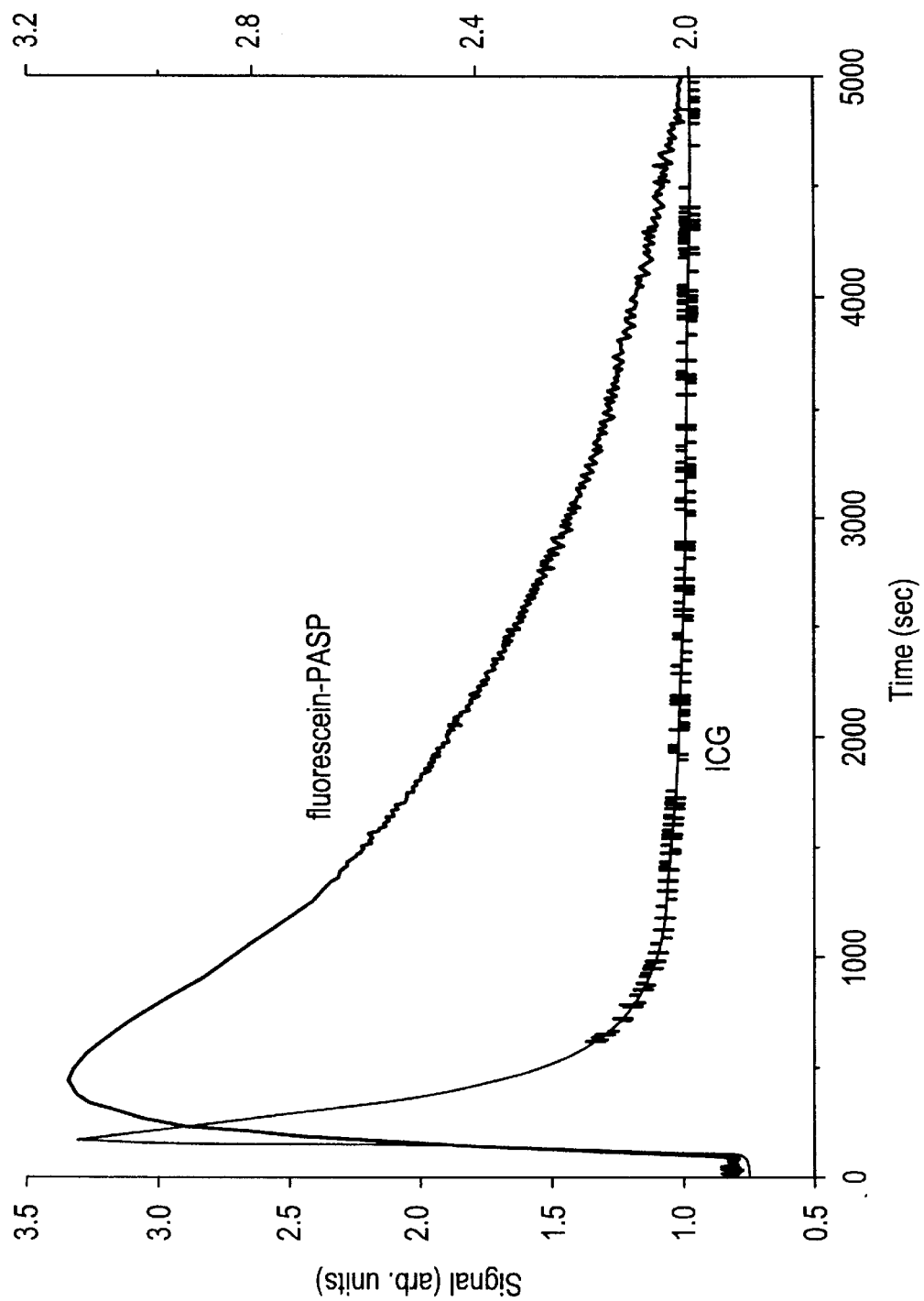
FIG. 4 shows the blood clearance profile in a normal rat of a mixture of indocyanine green dye and fluorescein-polyaspartic acid (MW 10,000) conjugate for the simultaneous assessment of liver and kidney function.

Use of a Combination of Detectable Agents to Simultaneously Measure Renal and Hepatic Functions Aqueous solutions of indocyanine green dye at 0.42 mg/mL and fluorescein-polyaspartic acid bioconjugate at 8 mg/mL were mixed together. This combined solution was injected intravenously into a rat and fluorescence was monitored from the ear. Incident light on the ear was at both 488 nm and 780 nm. Two detectors of fluorescent light were set at 520 nm and 830 nm. FIG. 4 shows the results. The two clearance curves are readily distinguishable. ICG is known to be cleared from the blood stream by the liver and fluorescein-polyaspartic acid is cleared by the kidney. The curves in FIG. 4 show the simultaneous measurement of both hepatic and renal function.

The utility of non-invasive fluorescence detection to monitor liver and kidney function has been established. The use of pulmonary artery catheters for monitoring mixed venous oxygen saturation has been well established, and use of a modified pulmonary artery catheter works similarly except that it is used to measure different physiological functions compared to the standard pulmonary artery catheters. The steps of the invention may be repeated in order to determine if physiological function is changing. Since many modifications, variations and changes in detail may be made to the described embodiments, it is intended that all matter in the foregoing description and shown in the accompanying drawings be interpreted as illustrative and not in a limiting sense.

What is claimed is:

1. A method of measuring at least two physiological activities wherein said activities are i) at least two activities of a single type of tumor tissue or organ or ii) at least one activity of each of at least two types of tumor tissues or organs in a patient's body, wherein said organ is a kidney, liver, brain or heart, comprising the steps of:
    a) administering into said patient's body fluid a detectable amount of at least two tracers selected from the group consisting of: i) chromophores or fluorophores capable of absorbing or emitting electromagnetic radiation of wavelength ranging from 400 to 900 nm, ii) paramagnetic agents, and iii) radiopharmaceuticals, with the proviso that at least one tracer is from group (i) or group (ii), wherein said tracers are selectively removed from said body fluid by said tissues or organs;
    b) detecting an amount of each of said tracers in said body fluid by measuring i) an absorption or emission of electromagnetic radiation for each of said chromophores or fluorophores that are used, ii) a magnetic signal produced by each of said paramagnetic agents that are used, and iii) a radioactive decay for each of said radiopharmaceuticals that are used, by using 1) at least one non-invasive surface monitoring probe, 2) at least one invasive endoscopic device or catheter capable of detecting said tracers, or 3) at least one non-invasive surface monitoring probe and at least one invasive endoscopic device or catheter capable of detecting one or more of said tracers;
    c) determining a clearance rate or a clearance profile for each of said tracers from said body fluid based on each tracer's amount in said body fluid detected in step (b); and
    d) correlating said clearance rate or profile of each tracer with one of said physiological activities of said organs or tissues,
    wherein said physiological activities result in i) accumulation of said tracers in said organ or tumor tissue, or ii) removal of said tracers from the blood;
    wherein at least two physiological activities are determined, further wherein at least two tracers are present simultaneously in said body fluid at detectable amounts at a time during step (b).

2. The method of claim 1 wherein said detecting is performed using a non-invasive surface monitoring probe.

3. The method of claim 1, wherein said detecting is performed using an invasive endovascular probe placed in a peripheral vein, a central vein or a pulmonary artery.

4. The method of claim 1, wherein said organs are liver and kidney.

5. The method of claim 1 wherein at least two tracers are administered simultaneously.

6. The method of claim 1 wherein at least one tracer is administered subsequently to administration of a first tracer.

7. The method of claim 1 wherein detecting of at least two tracers is performed simultaneously.

8. The method of claim 1 wherein detection of a first tracer is performed at a time separate from detection of a second tracer.

9. The method of claim 1 wherein said detecting is performed at multiple timepoints wherein detection of a first tracer is at timepoints different from timepoints of detection of a second tracer.

10. The method of claim 1 wherein said detecting is performed at multiple timepoints wherein detection of at least two tracers occurs simultaneously at at least one timepoint.

11. The method of claim 1 wherein steps (a) through (d) are repeated to determine if at least one of said physiological activities changes.

12. The method of claim 1 wherein said tracers are administered by injection.

13. The method of claim 1 wherein said tracers are administered by intravenous injection.

14. The method of claim 1 wherein said at least one body portion includes blood vessels near a surface of skin of said patient.

15. The method of claim 1 wherein said tracers comprise i) at least two chromophores, ii) at least two fluorophores, or iii) at least one chromophore and at least one fluorophore.

16. The method of claim 15 wherein said chromophores or fluorophores are selected from the group consisting of cyanines, indocyanines, squaraines, fluoresceins and polyanionic fluorescein bioconjugates.

17. The method of claim 15 wherein said fluorophores are selected from the group consisting of indocyanine green and fluorescein-polyaspartic acid bioconjugates.

18. The method of claim 1 wherein said detecting is performed by a fluorescence method.

19. The method of claim 1 wherein said detecting is performed by an absorbance method.

20. The method of claim 1 wherein said detecting is performed by a light scattering method.

21. The method of claim 1 wherein said tracers comprise at least two paramagnetic agents.

22. The method of claim 21 wherein said paramagnetic agents are selected from the group consisting of Gd-DTPA, Gd-DTPA-bis(methoxyethyl)amide and superparamagnetic iron oxide particles.

23. The method of claim 1 wherein said tracers comprise i) at least one radiopharmaceutical and ii) at least one chromophore or fluorophore.

24. The method of claim 23, wherein i) said radiopharmaceutical is selected from the group consisting of $^{99m}$Tc-DTPA, $^{51}$Cr-EDTA, $^{99m}$Tc-MAG3, $^{99m}$Tc-HIDA, $^{99m}$Tc-sestamibi, $^{99m}$Tc-tetrafosmin, $^{99m}$Tc-ECD, $^{131}$I-hippuran, $^{99m}$Tc-DTPA-octreotide and $^{99m}$Tc-DTPA-octreotate; and ii) said chromophore or fluorophore is selected from the group consisting of cyanines, indocyanines, squaraines, fluoresceins and polyanionic fluorescein bioconjugates.

25. The method of claim 1 wherein said tracers comprise i) at least one paramagnetic agent and ii) at least one chromophore or fluorophore.

26. The method of claim 25, wherein i) said paramagnetic agents are selected from the group consisting of Gd-DTPA, Gd-DTPA-bis(methoxyethyl)amide and superparamagnetic iron oxide particles and ii) said chromophores or fluorophores are selected from the group consisting of cyanines, indocyanines, squaraines, fluoresceins and polyanionic fluorescein bioconjugates.

27. The method of claim 1 wherein said tracers comprise i) at least one radiopharmaceutical and ii) at least one paramagnetic agent.

28. The method of claim 27, wherein i) said radiopharmaceutical is selected from the group consisting of $^{99m}$Tc-DTPA, $^{51}$Cr-EDTA, $^{99m}$Tc-MAG3, $^{99m}$Tc-HIDA, $^{99m}$Tc-sestamibi, $^{99m}$Tc-tetrafosmin, $^{99m}$Tc-ECD, $^{131}$I-hippuran, $^{99m}$Tc-DTPA-octreotide and $^{99m}$Tc-DTPA-octreotate and ii) said paramagnetic agent is selected from the group consisting of Gd-DTPA, Gd-DTPA-bis(methoxyethyl)amide and superparamagnetic iron oxide particles.

* * * * *